(12) United States Patent
Fleischer et al.

(10) Patent No.: US 11,744,712 B2
(45) Date of Patent: Sep. 5, 2023

(54) LORDOTIC ROD-WASHER IMPLANT FOR LUMBO-SACRAL FUSION

(71) Applicants: Gary Fleischer, Exeter, NH (US); Brandon Arthurs, Wilmington, NC (US); Ryan Arce, Denver, CO (US); Leighton LaPierre, Wilmington, NC (US); Jeffrey R. Schell, Denver, CO (US)

(72) Inventors: Gary Fleischer, Exeter, NH (US); Brandon Arthurs, Wilmington, NC (US); Ryan Arce, Denver, CO (US); Leighton LaPierre, Wilmington, NC (US); Jeffrey R. Schell, Denver, CO (US)

(73) Assignee: Gary Fleischer, Exeter, NH (US)

( * ) Notice: Subject to any disclaimer, the term of this patent is extended or adjusted under 35 U.S.C. 154(b) by 0 days.

(21) Appl. No.: 17/114,870

(22) Filed: Dec. 8, 2020

(65) Prior Publication Data

US 2021/0085477 A1    Mar. 25, 2021

Related U.S. Application Data

(62) Division of application No. 16/047,657, filed on Jul. 27, 2018, now Pat. No. 10,888,432.

(60) Provisional application No. 62/537,564, filed on Jul. 27, 2017.

(51) Int. Cl.
| | | |
|---|---|---|
| A61F 2/44 | (2006.01) | |
| A61F 2/30 | (2006.01) | |
| A61B 17/70 | (2006.01) | |
| A61B 17/86 | (2006.01) | |
| A61F 2/46 | (2006.01) | |
| A61B 17/02 | (2006.01) | |

(52) U.S. Cl.
CPC .......... *A61F 2/446* (2013.01); *A61B 17/7044* (2013.01); *A61B 17/7055* (2013.01); *A61B 17/8685* (2013.01); *A61F 2/30942* (2013.01); *A61F 2/4455* (2013.01); *A61F 2/4611* (2013.01); *A61B 17/8695* (2013.01); *A61B 2017/0256* (2013.01); *A61F 2002/3085* (2013.01); *A61F 2002/30405* (2013.01); *A61F 2002/30514* (2013.01); *A61F 2002/30622* (2013.01); *A61F 2002/4629* (2013.01); *A61F 2002/4677* (2013.01)

(58) Field of Classification Search
None
See application file for complete search history.

(56) References Cited

U.S. PATENT DOCUMENTS

| | | |
|---|---|---|
| 6,558,386 B1 | 5/2003 | Cragg |
| 6,899,716 B2 | 5/2005 | Cragg |
| 7,014,633 B2 | 3/2006 | Cragg |
| 7,608,077 B2 | 10/2009 | Cragg et al. |
| 7,727,263 B2 | 6/2010 | Cragg |

(Continued)

*Primary Examiner* — Tessa M Matthews
(74) *Attorney, Agent, or Firm* — Hall Estill Law Firm

(57) ABSTRACT

The preferred embodiment of the present invention is generally described as a lordotic pre-sacral rod implant, or implant construct, for use in association with spinal fusion procedures. In an embodiment, the lordotic pre-sacral rod implant incorporates a washer configured to press against the endplate of the L5 vertebral body and thereby force the vertebral bodies of the lumbosacral junction into a lordotic orientation.

10 Claims, 8 Drawing Sheets

(56) References Cited

U.S. PATENT DOCUMENTS

| | | |
|---|---|---|
| 8,034,055 B2 | 10/2011 | Cragg |
| 8,388,660 B1 * | 3/2013 | Abdou ............... A61B 17/8685 606/267 |
| 2002/0052608 A1 | 5/2002 | Kvarnstrom et al. |
| 2003/0212400 A1 * | 11/2003 | Bloemer ............ A61B 17/8685 606/279 |
| 2005/0113919 A1 | 5/2005 | Cragg et al. |
| 2006/0085075 A1 | 4/2006 | McLeer |
| 2006/0122597 A1 | 6/2006 | Jones et al. |
| 2008/0262502 A1 * | 10/2008 | Ainsworth ............ A61F 2/4611 623/17.12 |
| 2010/0168751 A1 * | 7/2010 | Anderson ............ A61B 17/142 606/86 A |
| 2011/0040329 A1 | 2/2011 | Ainsworth et al. |
| 2011/0046682 A1 | 2/2011 | Stephan et al. |
| 2012/0029518 A1 | 2/2012 | Blackwell et al. |

* cited by examiner

LORDOTIC ROD-WASHER IMPLANT FOR LUMBO-SACRAL FUSION

CROSS REFERENCE TO RELATED APPLICATIONS

The present application is a divisional application of U.S. Ser. No. 16/047,657, filed Jul. 27, 2018, entitled "LORDOTIC ROD-WASHER IMPLANT FOR LUMBO-SACRAL FUSION", which claims benefit under 35 U.S.C. § 119(e) of U.S. Provisional Patent Application Ser. No. 62/537,564 filed on Jul. 27, 2017; the entire contents of each of the above-referenced applications are hereby expressly incorporated herein by reference.

BACKGROUND OF THE INVENTION

A previously unsolved challenge remains associated with providing or creating lordosis with a spinal implant delivered via the pre-sacral approach.

The pre-sacral approach to surgically access the spine, as described in U.S. Pat. No. 8,034,055, which is incorporated by reference herein in its entirety, is beneficial as it allows a surgeon to fuse two or more vertebrae via a tissue-sparing, minimally invasive approach. Current methods and apparatuses are associated with the pre-sacral approach to accomplish spinal fusion, including those described in U.S. Pat. Nos. 6,558,386; 6,899,716; 7,014,633; 7,727,263; 7,608,077, which are incorporated by reference herein in their entirety. Such methods and apparatuses are generally shown to be highly effective in the literature at accomplishing spinal fusion. Studies have also shown that axial interbody fusion, utilizing the pre-sacral approach, supplemented with posterior fixation does not alter segmental or global lordosis in most patients. However, the current methods and apparatuses associated with the pre-sacral approach to accomplish spinal fusion lack mechanisms to create additional lordosis during placement. Inadequate lordosis after lumbar spine fusion can lead to chronic low back pain, positive sagittal balance with forward inclination of the trunk and adjacent segment degeneration. The preponderance of the evidence in the literature suggests that proper sagittal balance, featuring proper lordosis, remains a keystone for good outcomes following spinal fusion surgery. Therefore, an unmet need remains to incorporate mechanisms to create lordosis during spinal fusion surgery associated with the pre-sacral approach.

Previous implants delivered via the pre-sacral approach limits the ability of a surgeon to create lordosis during utilization of the pre-sacral approach. In part, this is because previous spinal implants delivered via the pre-sacral approach fail to change the angular relationship of the bones and allow the bones to rotate, inducing lordosis and restoring the balance of the spine. In addition, a previous prior art spinal implant delivered via the pre-sacral approach merely fixate the two vertebral bodies only prior to manipulating the vertebral bodies, and therefore can only translate one vertebral body relative to the other vertebral body along the axis of the implant. Moreover, previous implants adapted to create lordosis would associate with the problems of the implant loosening or backing down after placement. An unmet need, therefore, remains to create an implant able to be placed via the pre-sacral approach that improves surface area contact with the endplate of a vertebral body in a lockable fashion, thereby enabling the surgeon to manipulate the sagittal balance in addition to restoring the disc height by distracting the L5 and Si vertebral bodies away from each other.

Other attempted solutions for the problem of providing lordosis from the presacral approach have failed to meet one or more unsolved needs recognized by the inventor because of still-remaining challenges.

SUMMARY OF THE INVENTION

The preferred embodiment of the present invention is generally described as a lordotic pre-sacral rod implant, or implant construct, for use in association with spinal fusion procedures. In an embodiment, the lordotic pre-sacral rod implant comprises a Washer 2. In an embodiment, the Washer 2 incorporates with the lordotic pre-sacral rod implant near the distal end by surrounding a protrusion from the remaining mass, as depicted by FIG. 2. In an embodiment, the Washer 2 is configured to press against the endplate of the L5 vertebral body. In the preferred embodiment, the forces in the distal direction orient the Washer 2 against the endplate of the L5 vertebral body parallel to said endplate. Such configuration has been observed by the inventors to allow distraction to occur simultaneously with angular change and encourage an optimal lordotic arrangement of the vertebral bodies associated with the lumbosacral junction.

DETAILED DESCRIPTION

Figure 1:
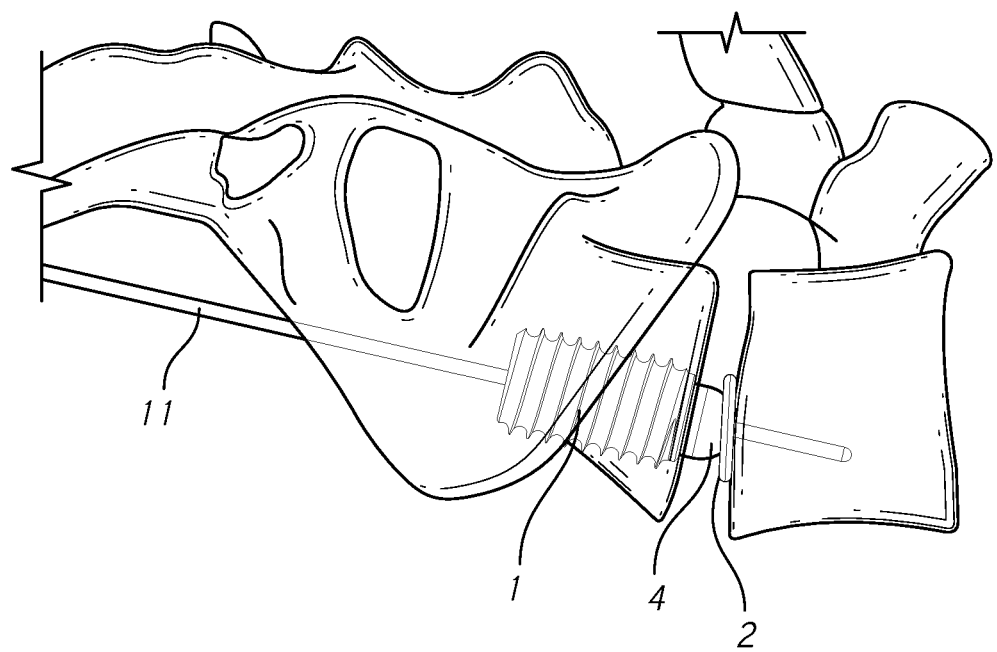
FIG. 1 depicts a sacrum anchor, a distraction rod, and a washer placed over a guide wire placed through a sacrum and into the L5 vertebral body in accordance with an embodiment of the invention.
Figure 2:
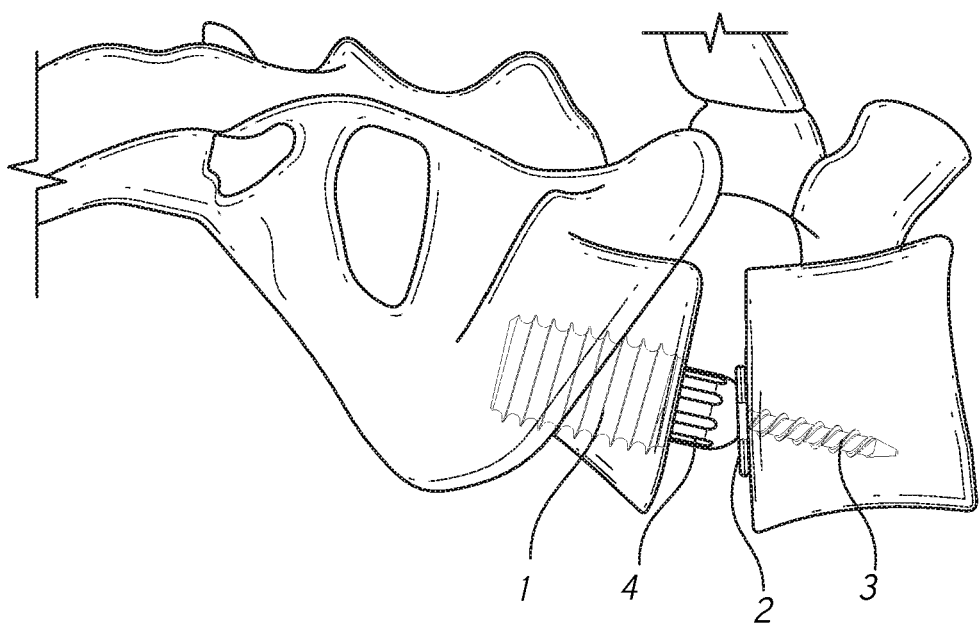
FIG. 2 depicts an embodiment of the fully assembled lordotic pre-sacral rod implant construct placed as intended into the lumbo-sacral junction following the creation of distraction and lordosis in accordance with an embodiment of the invention.

In the preferred embodiment, the lordotic pre-sacral rod implant functions by its Washer 2 configured to self-orient parallel to the endplate of the L5 vertebral body at an angle to the axis trajectory of the remainder of the implant, said axis trajectory defined by the Guide Wire 11 as placed during the preferred method of use, to encourage a lordotic configuration of the vertebral bodies, as depicted by FIG. 1. In an embodiment, a fully assembled lordotic pre-sacral rod implant as depicted in FIG. 2 is placed into the lumbosacral junction as the partially assembled lordotic pre-sacral rod implant as shown in FIG. 1.

Figure 5:
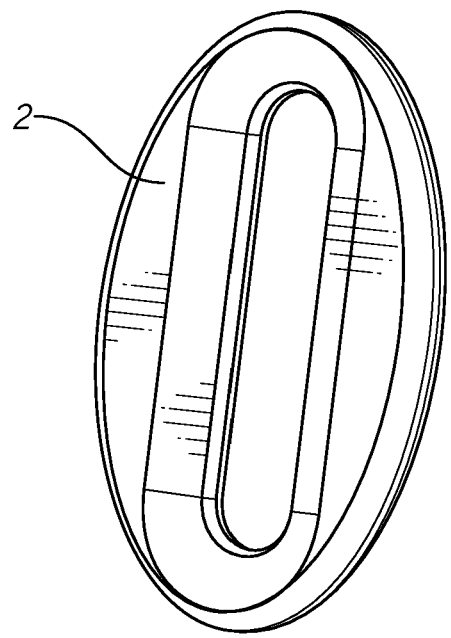
FIG. 5 depicts a washer in accordance with an embodiment of the invention.

An embodiment of the invention incorporates a Washer 2, as depicted in FIG. 5. The Washer 2 in an embodiment of the invention allows for increased surface area of contact between the mass of the implant and the endplate. The present inventors have recognized that the increased surface area enables broader distribution of the force transferred through the lordotic pre-sacral rod implant and placed against a L5 vertebral body endplate. The Washer 2 in the preferred embodiment of the invention described as a substantially flat oval-shaped washer. In an embodiment, the Washer 2 is expandable. In an embodiment, the mechanisms facilitating the expansion of the Washer 2 operate by slidably overlapping with one another. In an embodiment, the oval or circular shaped mass of the Washer 2 is subdivided into multiple sections, optionally into quadrants, and connectably linked by telescoping arms meeting at a central point to provide for expansion. The present inventors have recognized that expansion of the Washer 2 provides for increased surface area contact between the Washer 2 and the endplate of the L5 body and thereby is associated with numerous advantages, including minimization of the risk of subsidence.

Figure 4:
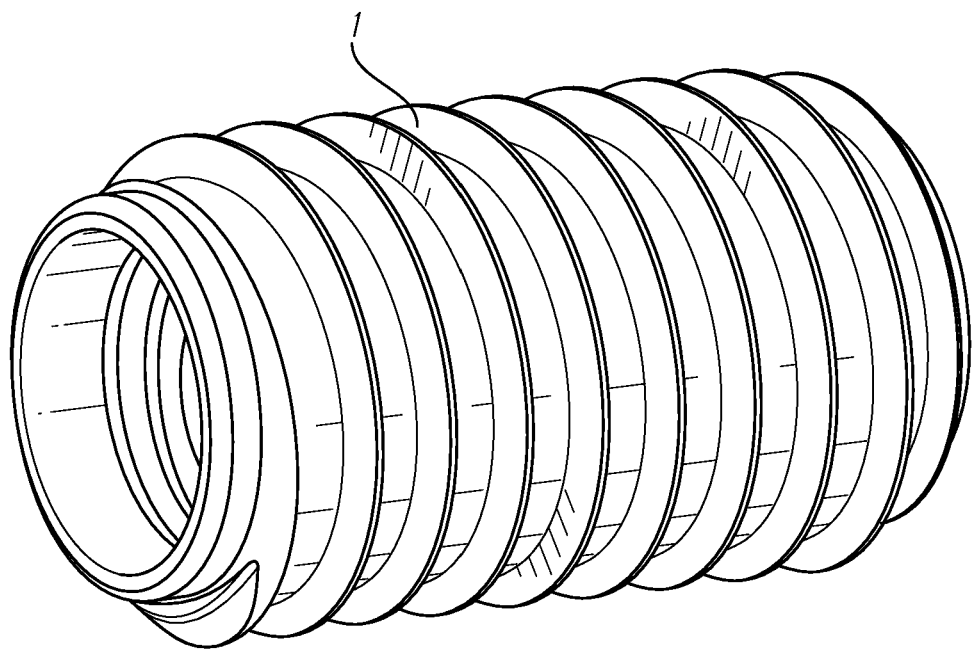
FIG. 4 depicts a sacrum anchor in accordance with an embodiment of the invention.

In an embodiment, the Washer 2 interacts with the lordotic pre-sacral rod implant near its distal end. In an embodiment, the interaction takes place via a screw-like protrusion traversing through an elongate aperture in the Washer 2, as shown in FIG. 4. In an embodiment, the aperture allows for the Washer 2 to be angled to conform to the plane of the L5 endplate while allowing the Fixation Screw 3 to pass through independent of the washer's angulation. An embodiment of the Washer 2 incorporates a guide slot, intended to guide the path for the guide pin to follow while the Distraction Rod 4 is moving through the Sacrum Anchor 1. The guide slot in an embodiment of the invention allows the Washer 2 to self-adjust to a plane that is parallel to the L5 endplate. A guide slot in an embodiment of the invention is also described as a feature in the Washer 2 that allows the Washer 2 to extend radially beyond the outer diameter of the Sacrum Anchor 1 in order to increase the footprint of the mass of the implant.

The present inventors have recognized the inherent advantage of an increase in surface area pushing upon the L5 vertebral body, such surface area thereby dispersing force against the L5 vertebral body, which thereby minimizes the risk of subsidence. An embodiment of the Washer 2 incorporates a recessed chamfer. The recessed chamfer as depicted in FIG. 5 provides a guide-path boundary for the Distraction Rod 4 to slidably and rotationally engage with the Washer 2.

Figure 3:
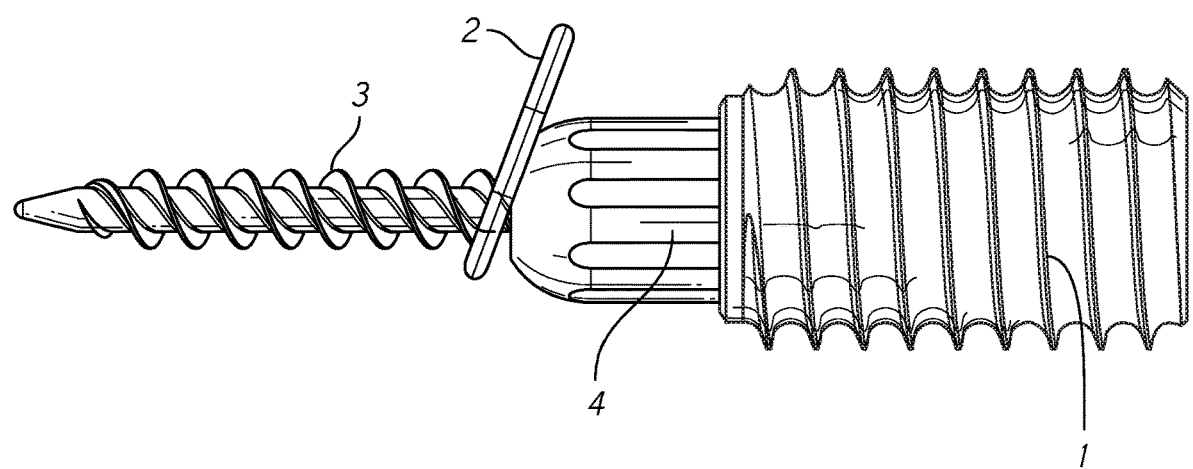
FIG. 3 depicts an embodiment of the fully assembled lordotic pre-sacral rod implant construct in accordance with an embodiment of the invention.

An embodiment of the invention incorporates a Sacrum Anchor 1, as depicted by FIG. 3. In various embodiments, the Sacrum Anchor 1 varies in lengths ranging from 20 millimeters through 50 millimeters to accommodate different sacral anatomies. In the preferred embodiment, the Sacrum Anchor 1, consists of titanium in its composition. An embodiment of the Sacrum Anchor 1 incorporates custom bone threads on its external surface. In an embodiment the custom bone threads are configured as depicted by FIG. 3. In the preferred embodiment, the custom bone threads increase bone purchase and resist subsidence or push out within the bone.

Figure 13:
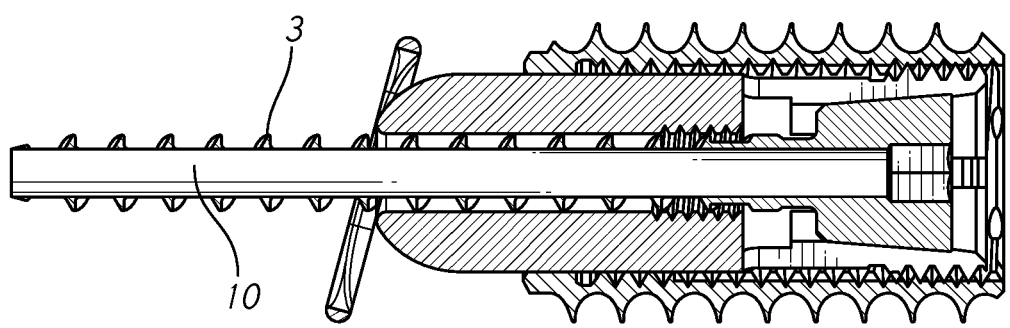
FIG. 13 depicts an alternative cross-sectional view of an implant in accordance with an embodiment of the invention.
Figure 14:
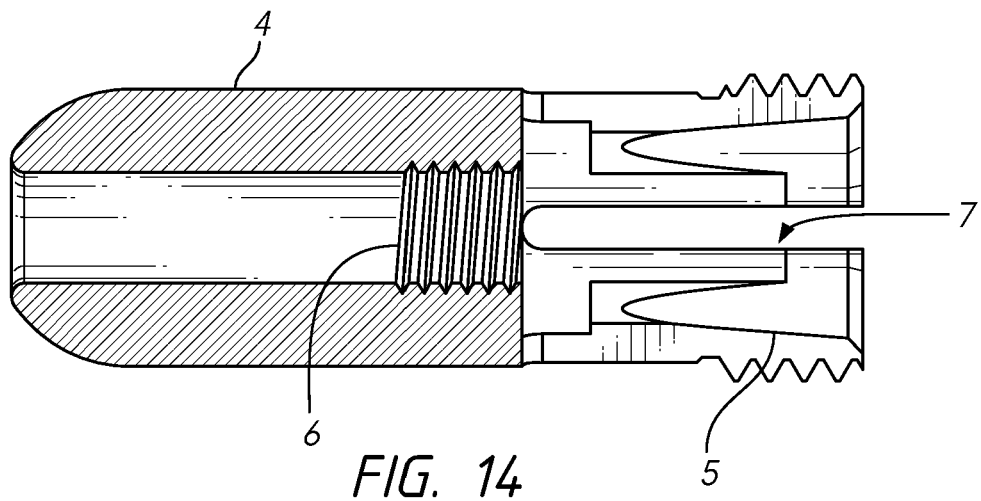
FIG. 14 depicts a cross sectional view of the distraction rod in accordance with an embodiment of the invention.

The Sacrum Anchor 1, in an embodiment of the invention, comprises an externally threaded rod having an aperture within. An embodiment of the Distraction Rod 4 configured to pass through the aperture of the Sacrum Anchor 1 comprises a Tapered Cut 5, defining the boundary of the aperture therein, as depicted in FIG. 13. In an embodiment, the Tapered Cut 5 features an inward 5' taper from the proximal end of the Distraction Rod 4 to the point of the Internal Hex Drive Feature 9. In an embodiment, the aperture has a circular cross section. In the preferred embodiment, the aperture having a circular cross section has a diameter of approximately 0.3350 inches at the proximal end, with a progressively smaller diameter as the aperture progresses distally in accordance with the 5' taper to the endpoint of the Tapered Cut 5, as depicted in FIG. 13 and FIG. 14. Various embodiments may feature a Tapered Cut 5 and corresponding aperture featuring different angles of taper or different diameters without departing from the scope of the invention.

An embodiment of the Sacrum Anchor 1 comprises a specially configured bone thread on the external surface, as depicted in FIG. 3. In the preferred embodiment, the Sacrum Anchor 1 features a 15.5 millimeter major thread diameter.

The Sacrum Anchor 1 in an embodiment of the invention comprises an internal drive feature. In an embodiment, the internal drive feature is configured to correspond to the dimensions of the distal end of a driver. In an embodiment, the driver comprises dimensions of standard form as recognized by one skilled in the art in association with surgical uses. In such embodiment, the internal drive feature is configured to allow a driver to attach in order to rotate the anchor. Further, the driver utilized in association with the internal drive feature is thereby able to deliver the Sacrum Anchor 1 to and into a hole through a sacral bore previously created by the surgeon to accommodate the placement of the lordotic pre-sacral rod implant in the proper position in accordance with methods more precisely described in U.S. Pat. No. 8,034,055, which is incorporated by reference herein in its entirety.

Figure 10:
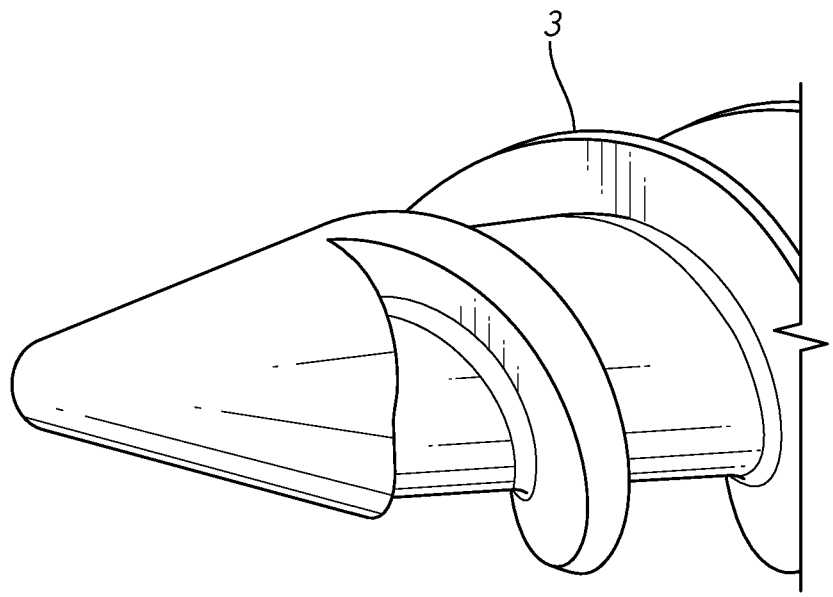
FIG. 10 depicts the self-drilling distal end of a fixation screw in accordance with an embodiment of the invention.
Figure 11:
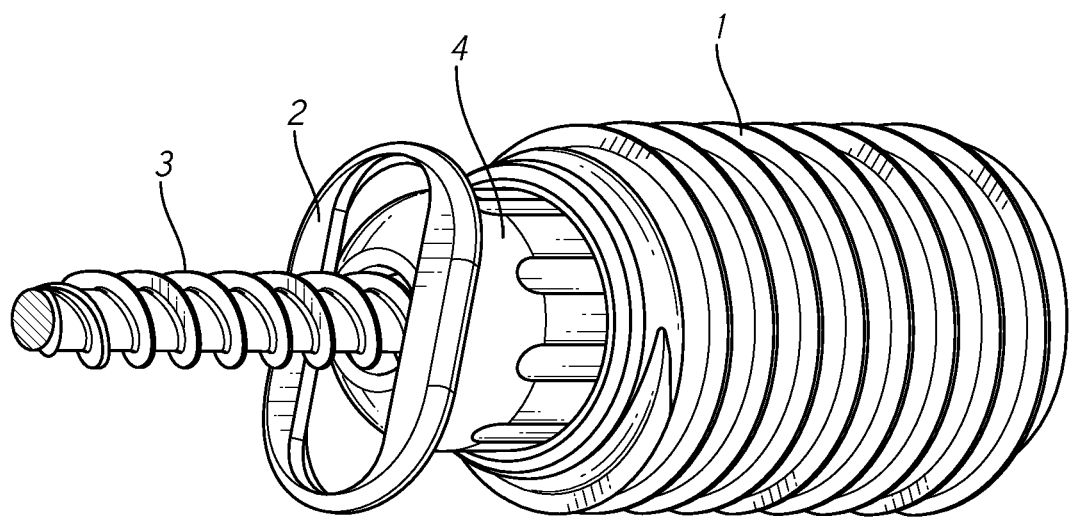
FIG. 11 depicts a distal perspective view of an implant in accordance with an embodiment of the invention.
Figure 12:
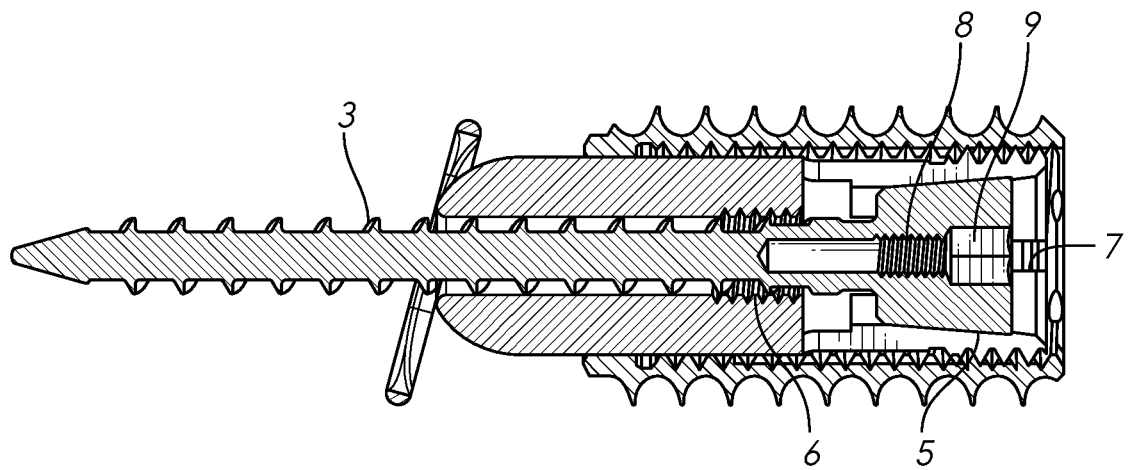
FIG. 12 depicts a cross-sectional view of an implant in accordance with an embodiment of the invention.

An embodiment of the Sacrum Anchor 1 incorporates internal threading configured to mate with the Distraction Rod 5. The internal threading configured to mate with the Distraction Rod 5 in an embodiment of the invention is described as female threads intended to mate with the corresponding male threads on the Distraction Rod 4 as depicted in FIG. 10. Such internal threading configured to mate with the Distraction Rod 5 in an embodiment of the invention are configured to enable the Distraction Rod 4 to be controllably advanced axially relative to the Sacrum Anchor 1 via a screwing motion.

An embodiment of the Sacrum Anchor 1 comprises Distraction Rod Internal Retention Threads 6, as depicted in FIG. 13. The Distraction Rod Internal Retention Threads 6 in an embodiment consist of standard 10-32 2B threads, as recognized by one skilled in the art. In an embodiment, the Distraction Rod Internal Retention Threads 6 are configured to engage with threading on the external surface of the driver. In an embodiment, the Distraction Rod Internal Retention Threads 6 are configured to interact with the Distraction Rod 4 to hold the Distraction Rod 4 in a retained position during insertion. In an embodiment, the retention of the Distraction Rod 4 via the interaction of the driver and the Distraction Rod Internal Retention Threads 6 allows for the attachment of the driver via a screwing motion and the detachment of the driver via an unscrewing motion.

An embodiment of the invention comprises Fixation Screw Internal Retention Threads 8, as depicted in FIG. 3. In an embodiment, the Fixation Screw Internal Retention Threads 8 consist of standard 2-56 2B threads. In an embodiment, the threads are configured to engage with the driver. In an embodiment, the interaction between the threads and the driver function to lock the Fixation Screw 3 during insertion.

Figure 6:
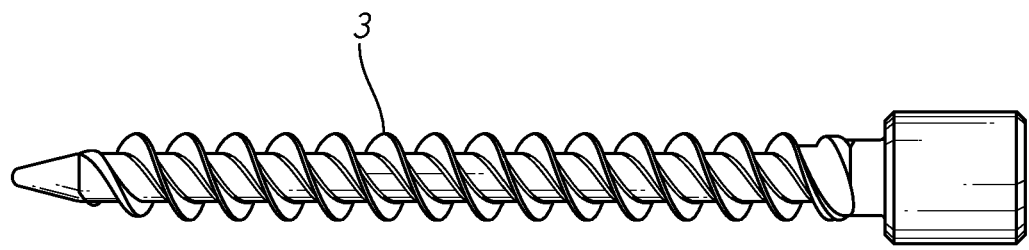
FIG. 6 depicts a fixation screw in accordance with an embodiment of the invention.
Figure 7:
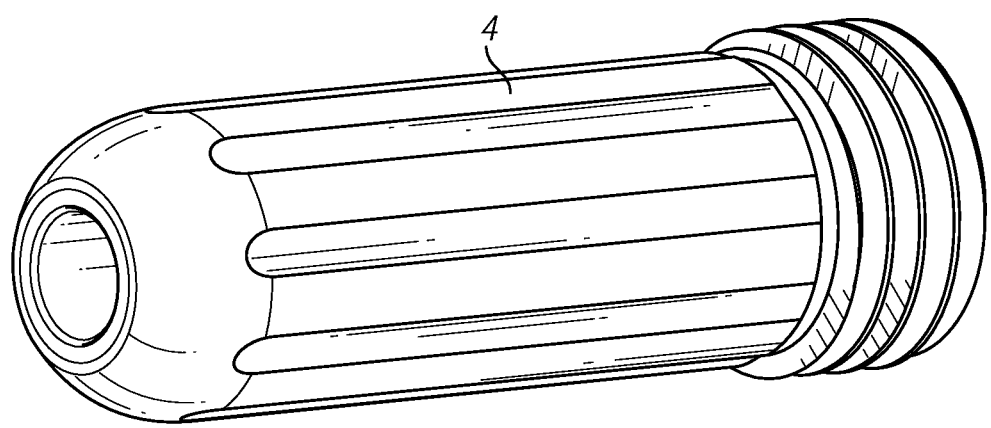
FIG. 7 depicts a distraction rod in accordance with an embodiment of the invention.

An embodiment of the invention incorporates a Fixation Screw 3, as depicted by FIG. 6. The Fixation Screw 3 in an embodiment of the invention is described as threaded screw configured to be fixated within the L5 vertebral body. The Fixation Screw 3 in an embodiment of the invention is also described as a secondary screw that passes through an opening defining a path through the Sacrum Anchor 1, Distraction Rod 4, and Washer 2 to fixate the L5 vertebral body relative to the angle and position of the sacrum accomplished by the placement of the lordotic pre-sacral rod implant. In an embodiment, the Fixation Screw 3 is configured to affix within the L5 vertebral body along the same path that the Guide Wire 11 establishes into the L5 vertebral body. An example of the path that the Guide Wire 11 establishes into the L5 vertebral body is depicted in FIG. 1. In an embodiment, the Fixation Screw 3 further comprises a cannulation. The cannulation is configured to allow for delivery of the Fixation Screw 3 over the Guide Wire 11 during the preferred method of use. In the preferred embodiment, the cannulation travels along the major axis of the Fixation Screw 3 in its center. In an embodiment, the cannulation is 0.092 inches in diameter. The preferred embodiment of the Fixation Screw 3 comprises the following dimensions: 45 mm in length with a 4.5 mm major thread diameter. The preferred embodiment of the Fixation Screw 3 consists of titanium. A Fixation Screw 3 in an embodiment of the invention is also described as having a driving feature on the proximal end that engages with a driver in accordance with methods and mechanisms readily apparent to one skilled in the art. In the preferred embodiment, the proximal end of the Fixation Screw 3 abuts an internal taper feature located on the inside of the Distraction Rod 4. This internal feature lags the L5 vertebral body onto the implant construct as the surgeon uses tools to tighten the assembled implant construct. In an embodiment, the Fixation Screw 3 features an aggressive self-drilling tip located on the distal end of the Fixation Screw 3 to easily drill into the vertebral body. An embodiment of the Fixation Screw 3 comprises a driver connection. The preferred embodiment of the driver connection comprises the dimensions associated with standard Torx connection sizing as recognized by one skilled in the art. In an embodiment, the driver connection is configured to accommodate the application of a Torx drive to the head of the Fixation Screw 3 to interface with a delivery instrument. In an embodiment, the Fixation Screw 3 comprises an internal hex drive feature configured to allow for a hex driver to controllably advance the Fixation Screw 3. In an embodiment, the internal hex drive feature is configured to incorporate a 3 millimeter hex receptacle. In varying embodiments, the internal hex drive feature is of an increased size to facilitate more advancement torque. In the preferred embodiment, the Fixation Screw 3 comprises a thread with a major diameter of approximately 4 millimeters. In alternative embodiments, the Fixation Screw 3 comprises a thread with a major diameter of 5 millimeters or 6 millimeters. In varying embodiments, the internal dimensions of the Distraction Rod 4 vary to allow for passage of a Fixation Screw 3 of varying major diameters.

An embodiment of the invention incorporates a Distraction Rod 4, as depicted by FIG. 6. The Distraction Rod 4 in an embodiment comprises a proximal thread designed to threadedly engage with threading within the aperture of the Sacrum Anchor 1. The preferred embodiment of the Distraction Rod 4 comprises the following dimensions: 0.4 inches in diameter and 1.2 inches in length. In the preferred embodiment, the Distraction Rod 4 consists of titanium. The Distraction Rod 4 in an embodiment of the invention is described as a hollow cylindrical piece with a blunt and/or rounded tip. In the preferred embodiment, the Distraction Rod 4 is intended to be utilized as follows: as the Distraction Rod 4 is rotated relative to the Sacrum Anchor 1, the thread interaction causes the Distraction Rod 4 to advance in a distal direction toward the L5 vertebral body. The blunt and/or rounded tip of Distraction Rod 4 applies force upon the Washer 2 as it is advanced to increase the distance between the L5 vertebral body and the sacrum. Thereby, the advancement of the Distraction Rod 4 when utilized as intended by the inventors helps a surgeon to establish the lordotic angle of the lumbosacral junction. The blunt tip of the Distraction Rod 4 allows for a change in angulation relative to the Washer 2 as it pushes on the L5 endplate. When utilized by a surgeon in accord with the intended method of use, the Washer 2 self-aligns so it is substantially parallel with the plane of L5 endplate.

Figure 15:
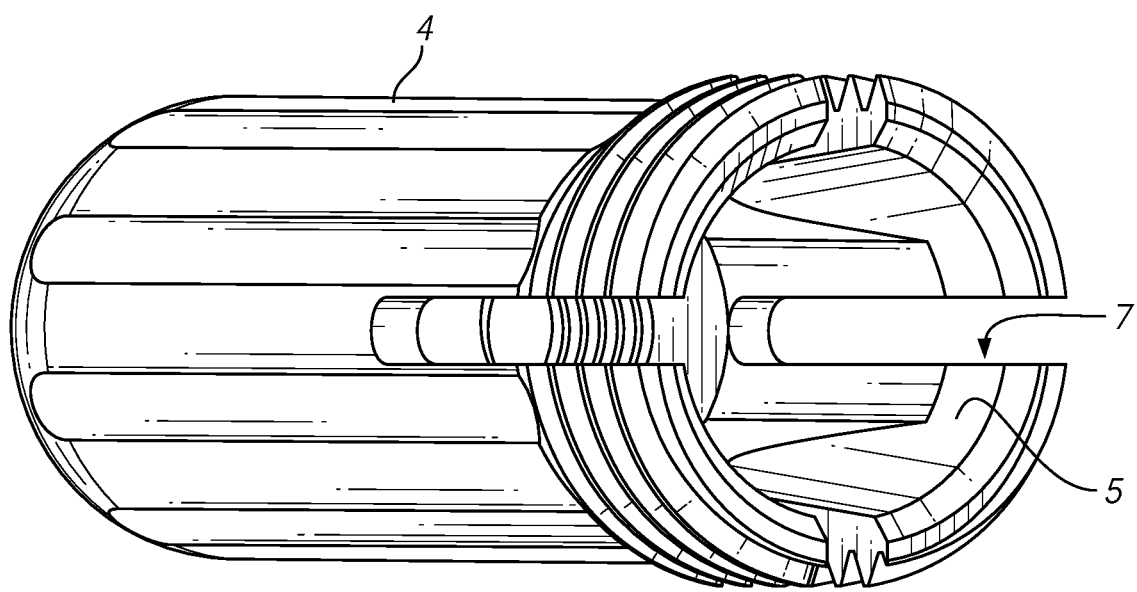
FIG. 15 depicts a proximal perspective view of the distraction rod in accordance with an embodiment of the invention.

An embodiment of the Distraction Rod 4 further comprises one or more Relief Cuts 7, as depicted in FIGS. 14 and 15. In an embodiment, optionally, the Relief Cuts 7 are described as slotting to allow for a reduction of friction between the outer surface of the Distraction Rod 4 and the inner surface of the Sacrum Anchor 1. In an embodiment, the Relief Cuts 7 provide for proximal end radial expansion to lock the distraction rod into the Sacrum Anchor 1 when the Fixation Screw 3 acts as the inserter according to methods and procedures as recognized by those skilled in the art. In an embodiment, the female taper feature located on the inside of the Distraction Rod 4 is configured to mate with the male feature of the proximal end of the Fixation Screw 3 to create a wedge or ramp to push out radially and expand the proximal end of the Distraction Rod 4. In an embodiment, the Relief Cuts 7 are configured to facilitate such expansion. The present inventors have discovered that the reduced friction during rotation helps to prevent the Sacrum Anchor 1 from inadvertently advancing in an unintended manner. The Relief Cuts 7 allow for flexion of the proximal end of the Distraction Rod 4. In an embodiment, the Relief Cuts 7 provide for fixation between and among the Distraction Rod 4 and the Sacrum Anchor 1. In an embodiment, the Distraction Rod 4 comprises 4 Relief Cuts 7.

An embodiment of the Distraction Rod 4 incorporates proximal threading, consisting of male threads of the specific dimensions to mate with the female threads of the Sacrum Anchor 1. The proximal threading is configured to allow the Distraction Rod 4 to controllably move relative to the Sacrum Anchor 1.

An embodiment of the Distraction Rod 4 incorporates a blunt round tip, as shown in FIG. 6. The blunt round tip is described as the distal end of the Distraction Rod 4 with a shape corresponding to the contours of the recessed chamfer of the Washer 2, as depicted in FIG. 4, to facilitate a sliding interface of the Distraction Rod 4 with the Washer 2. The sliding interface as intended by the inventors between the Distraction Rod 4 and the Washer 2 in the preferred embodiment is depicted in FIG. 2.

Figure 8:
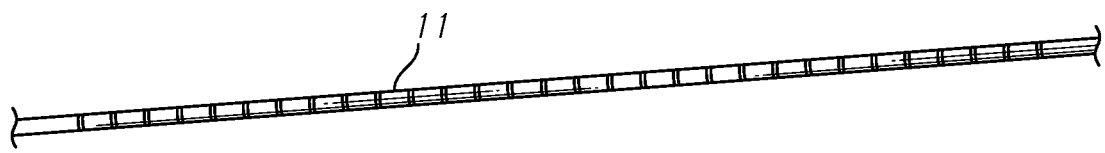
FIG. 8 depicts a guide wire in accordance with an embodiment of the invention.
Figure 9:
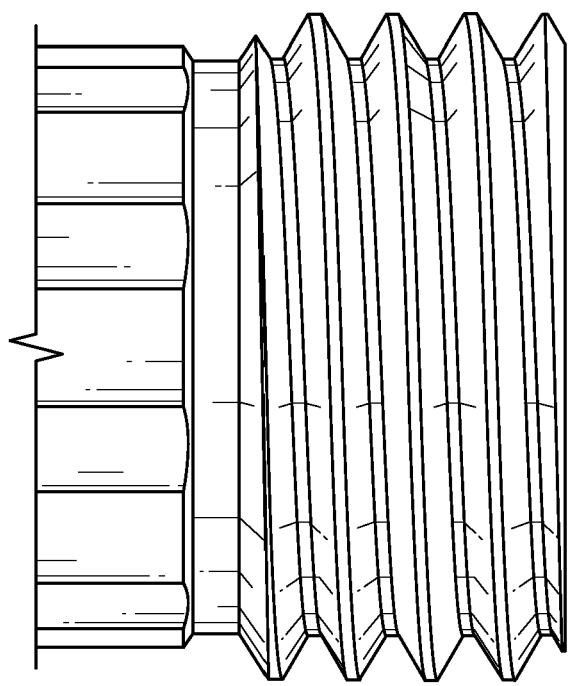
FIG. 9 depicts the proximal end of a distraction rod featuring threading in accordance with an embodiment of the invention.

An embodiment of the invention incorporates a Guide Wire 11, as depicted by FIG. 8. The preferred embodiment of the Guide Wire 11 comprises the following dimensions: 2.3 mm in diameter and 28" in length. The preferred embodiment of the Guide Wire 5, incorporates medical grade Stainless Steel and/or nitonol in its composition. The Guide Wire 11 incorporates a Blunt Guide Wire Tip. The Blunt Guide Wire Tip in an embodiment of the invention enables a surgeon to controllably advance the wire though bone. In an embodiment, the Guide Wire 11 incorporates Depth Markings. The Depth Markings are described as strategically located laser marks etched into the Guide Wire to indicate the depth level to which the Guide Wire 11 has advanced.

The present inventors have identified a preferred method of use associated with embodiments of the present invention. In the preferred embodiment, the method of use associated with a preferred embodiment of the implant results in the vertebral bodies comprising the lumbo-sacral junction to position into a lordotic orientation. Elements of the method of use are more precisely described in U.S. Pat. No. 8,034,055, which is incorporated by reference herein in its entirety. The preferred method of use additionally and/or separately comprises the following steps:

Defining a path to and through the sacrum by use of a Guide Wire 11, optionally on a path generally resembling that depicted in FIG. 1.

Inserting the Sacrum Anchor 1 into the sacrum over the Guide Wire 11, optionally by utilizing the internal drive features of the Sacrum Anchor 1.

Aligning the Washer 2 and Distraction Rod 4, optionally by threading and/or placement over the Guide Wire 11.

As the Distraction Rod Internal Retention Threads 6 hold the Distraction Rod 4 in a retained position during insertion, advancing the Washer 2 and Distraction Rod 4 together over the Guide Wire 11, through the Sacrum Anchor 1 as previously placed into the sacrum, and into the disc space.

With the Washer 2 captured by the Guide Wire 11, advancing the Distraction Rod 4 into and through the disc space until the distal end contacts and pushes the Washer 2 against the inferior surface of the L5 vertebral body. In an embodiment, the Guide Wire 11 must be removed or pulled back at this step. In an embodiment, the Guide Wire 11 must be removed at this point so that it is not fully engaged and fixated into the L5 body prior to or during this step.

Threading the Distraction Rod 4 through the Sacrum Anchor 1 to advance the Distraction Rod 4, thereby causing the Distraction Rod 4 to slide anteriorly against the Washer 2, transferring force upon the L5 vertebral body to distract and/or create lordosis within the L5-S1 spinal segment. Such step results in the orientation of the bodies of the lumbo-sacral junction into a lordotic state.

Once the desired lordosis and/or distraction is achieved, continue with one of the following:

While keeping the Guide Wire 11 in place, delivering the Fixation Screw 3 comprising a cannulation over the Guide Wire 11, through the Distraction Rod 4 until the proximal screw head engages with the proximal internal cut of the Distraction Rod 4. Alternatively, in an embodiment where the Fixation Screw 3 lacks a cannulation, removing the Guide Wire 11 and delivering the Fixation Screw 3 through the Distraction Rod 4.

In an embodiment, the Fixation Screw Internal Retention Threads 8 provide for the Fixation Screw 3 to be retained to the driver during delivery. Because of the Relief Cuts 7 in the Distraction Rod 4, outward flexing of the proximal threaded portion of the Distraction Rod 4 creates a lock between the outside of the Distraction Rod 4 and the inside of the Sacrum Anchor 1. Thereby, an additional step of locking the Outside of the Distraction Rod 4 and the inside of the Sacrum Anchor 1 may be achieved. Such configuration prevents any loss of the distraction and/or lordosis created within the disc space via the methods described herein. The Fixation Screw 3 may be torqued to a required torque to prevent backout. The Guide Wire 11 may then be removed if it has not already been removed.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover, in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art. The terms "coupled" and "linked" as used herein is defined as connected, although not necessarily directly and not necessarily mechanically. A device or structure that is "configured" in a certain way is configured in at least that way, but may also be configured in ways that are not listed. Also, the sequence of steps in a flow diagram or elements in the claims, even when preceded by a letter does not imply or require that sequence.

What is claimed is:

1. An implant, the implant comprising:
   a sacrum anchor;
   a distraction rod extending from the sacrum anchor and disposed at least partially within the sacrum anchor;
   a fixation screw extending through the distraction rod, the fixation screw secured directly to a part of a patient's body when the implant is fully implanted in the patient's body; and
   a washer disposed around the fixation screw and adjacent to the distraction rod.

2. The implant of claim 1, the distraction rod configured to be controllably advanceable relative to the sacrum anchor via a screwing motion.

3. The implant of claim 1, the washer includes an elongated slot.

4. The implant of claim 3, the elongated slot having a beveled edge.

5. The implant of claim 4, the distraction rod further comprising a tip having a shape corresponding to the beveled edge of the washer.

6. The implant of claim 1, the distraction rod configured to apply force upon the washer as it advances distally to cause the washer to press upon the L5 vertebral body.

7. The implant of claim 1, the sacrum anchor further comprising custom bone threads.

8. The implant of claim 1, the distraction rod further comprising a tapered cut.

9. The implant of claim 1, the distraction rod further comprising internal retention threads.

10. The implant of claim 1, configured to fixate in a position such that the forces placed upon the L5 vertebral body via the washer hold the vertebral bodies comprising the lumbo-sacral junction in a lordotic orientation.

* * * * *